United States Patent [19]

Gradl

[11] Patent Number: 5,713,987
[45] Date of Patent: Feb. 3, 1998

[54] METHOD AS WELL AS ACTIVE SUBSTANCE FOR PREVENTING MICROBIAL GROWTH ON SURFACES, AS WELL AS COMPOUND FOR SURFACE COATING OR FINISHING

[76] Inventor: Toni Gradl, Weisholz 3, D-Rattenberg, Germany

[21] Appl. No.: 577,871

[22] Filed: Dec. 22, 1995

[30] Foreign Application Priority Data

Dec. 22, 1994 [DE] Germany .................. 44 45 881.9

[51] Int. Cl.⁶ .................. A01N 25/00; C09D 5/14
[52] U.S. Cl. .................. 106/16; 106/15.05; 424/617; 424/639; 424/646; 523/122; 428/402; 428/403
[58] Field of Search .................. 106/16, 15.05; 424/78.09, 617, 639, 640, 646; 523/122; 502/324, 326; 428/402, 403

[56] References Cited

U.S. PATENT DOCUMENTS

| | | | |
|---|---|---|---|
| 5,266,105 | 11/1993 | Tsuneta et al. | 523/122 |
| 5,284,682 | 2/1994 | Martin | 427/386 |

FOREIGN PATENT DOCUMENTS

| | | |
|---|---|---|
| 0247019 | 11/1987 | European Pat. Off. |
| 0427858 | 5/1991 | European Pat. Off. |
| 0552071 | 1/1992 | European Pat. Off. |
| 2361157 | 8/1974 | Germany |
| 2752773 | 9/1991 | Germany |
| 63-79719 | 4/1988 | Japan |
| 2-96508 | 4/1990 | Japan |
| 4275376 | 9/1992 | Japan |
| 4288006 | 10/1992 | Japan |
| 4325571 | 11/1992 | Japan |
| 5-1245 | 1/1993 | Japan |
| 5-78218 | 3/1993 | Japan |

OTHER PUBLICATIONS

Chemical Abstracts, vol. 113, 1990, Ref. Nr. 2005f.

*Primary Examiner*—Anthony Green
*Attorney, Agent, or Firm*—Bierman, Muserlian and Lucas

[57] ABSTRACT

For preventing microbial growth on surfaces, there is proposed a method for the application of a growth-inhibiting substance, as well as a substance which has as active ingredient a stone flour with a catalyst precipitated on or bound to the latter as active substance. The catalyst is at least one substance of the group including brownstone (manganous oxide), finely divided elementary palladium and finely divided elementary ruthenium.

18 Claims, No Drawings

METHOD AS WELL AS ACTIVE SUBSTANCE FOR PREVENTING MICROBIAL GROWTH ON SURFACES, AS WELL AS COMPOUND FOR SURFACE COATING OR FINISHING

The invention relates to a method for preventing microbial growth on a surface by applying or making available a substance inhibiting or preventing such growth on or at the surface to an active substance that prevents growth of microorganisms on surfaces and to a compound such as varnish, paint, coating compound or similar compound for surface treatment or finish, having an active substance admixed with the compound for preventing the growth of microorganisms on surfaces.

Preventing microbial growth on surfaces is of great technical and economic importance. Thus, for example, bulwarks and other surfaces, including those of concrete and metal, for example in hydraulic structures or even drinking water and industrial water tanks, as well as other elements such as sails, nets or structures consisting of cork and rubber, very quickly become coated with a slimy layer of microorganisms, which acts as a base for the growth of additional organisms. This leads to destruction of the material and to corrosion, etc. Especially in ships, this leads to an increase in drag resistance in the water and hence to an increase in fuel consumption. Many other objects, such as textiles or seeds, must likewise be protected against microbial attack.

It is therefore known in principle that coatings, paints or varnishes, finishes (particularly in textiles), dressings (particularly on seeds), etc. with which an active substance which acts to inhibit growth or kill microorganisms is admixed may be used for protection against microbial growth. Until now these have been toxic substances whose release to the environment is polluting but cannot be prevented. For these reasons, the use of such active substances is often restricted and, in many areas, actually prohibited.

The object of the invention is to provide a method by which prevention of microbial growth on surfaces of structures to be protected is possible without the use of toxic substances. A method has been developed to accomplish this object. This method can be defined as a method for preventing microbial growth on a surface by applying or making available to the surface an active substance which inhibits or prevents the growth of the microbe on or at the surface. The active substance comprises a mineral flour having at least one catalyst which has been precipitated on or bound to the mineral flour. The catalyst is a brownstone (manganese dioxide), a finely divided elementary palladium, or a finely divided elementary ruthenium. According to the invention, the active substance for preventing microbial growth on surfaces is a mineral flour having a catalyst precipitated on or bound to the mineral flour wherein the catalyst has at least one substance of the group brownstone (manganese dioxide), finely divided elementary palladium, or finely divided ruthenium. A compound for surface coating (surface sealing) or surface finishing has also been developed. This surface coating compound is a varnish, a paint, a coating compound, or similar compound which is used for surface treatment or finishing in which the active substance has been admixed into the varnish, paint, coating compound, or other similar compound.

The active substance for inhibiting or preventing growth is applied to the surface to be protected in a great variety of ways. Specifically, said active substance is applied to the surface to be protected as a constituent of a paint, a lacquer, a coating compound, a finish (including a textile finish) as well as a dressing (including for dressing seeds). Alternatively, the active substance is applied to the surface to be protected by being admixed with the compound of which the structure to be protected is made of.

Varnishes, coatings, etc., which contain the active substance according to the invention are suitable for exterior finishes or coatings of ship and boat hulls, as underwater coatings of structures, as well as for coating storage tanks. In addition, the active substance is used in wood preservatives which are applied to wood, as well as in dressings applied to seeds. The varnishes, coatings, etc. which contain the active substance are formed by admixing the active substance with the varnishes and coatings.

In the invention suitable mineral flour includes at least one substance of the group montmorillonite kaolin basalt flour diabase flour phonolite flour granite-gneiss flour granite pegmatite meal In a preferred embodiment, the mineral flour treated with the catalyst is admixed with a resin to form a resinous emulsion. The resin is at least one resin of the group copal resin dammar resin shellac resin colophonium resin sandarac resin phenol-formaldehyde resin urea-formaldehyde resin melamine-formaldehyde resin alkyd resin polyester resin epoxy resin The invention provides effective prevention of microbial growth on surfaces, without the use of toxic substances.

The active substance can also be combined with a synthetic material or a rubber compound used in the production of products.

In a special embodiment the invention relates to a compound for surface coating or finishing which contains a percentage of the active substance in admixed form, where the percentage of active substance amounts for example to about 5 to 25 weight percent, referred to 100 weight percent of the total compound.

The invention and its effectiveness will be explained in greater detail by way of the following examples.

EXAMPLE I

In this example brownstone (manganese dioxide) was precipitated from potassium permanganate, by reduction, on montmorillonite. The powder obtained was dried. This powder (active substance) was added in a percentage of 5 weight percent to a nutrient agar (1.5% agar, Merck nutrient broth) and poured into a first group of Petri dishes. This agar, without the active substance, was placed in a second group of Petri dishes as control specimen. In both cases, the agar was sterilized or autoclaved in every instance.

After solidifying, all dishes were inoculated with a culture of Bacillus subtilis with the use of an inoculating loop (smear method). The dishes were incubated at 20° C. Growth was assessed in a comparison of the dishes with and without the active substance after 24 hours, 48 hours and 72 hours. Except for an initial growth, the Bacillus subtilis culture in the dishes with the active substance failed to develop, while the culture in the control dishes multiplied fully.

This result was evidently attributable to the fact that the microorganisms avoid contact with the catalyst distributed in or on the mineral flour.

EXAMPLE II

In this example a cold-setting two-component epoxy varnish was mixed with ten weight percent of a brownstone precipitated on montmorillonite (intermixed with a natural resinous emulsion) and applied to glass slides. After solidifying, the slides were placed in a beaker with nutrient broth. The nutrient solution or broth had been inoculated four days previously with a suspension of earth. Glass slides which had likewise been coated with epoxy varnish, but without the active substance, were used as comparison or control specimens. The slides were incubated at 25° C. After 24, 48 and 96 hours, the coated glass slides were compared. While the controls had become coated with a slimy layer after 48 and 96 hours, no such growth was observed on the glass slides coated with epoxy varnish and active substance.

I claim:

1. A method for preventing microbial growth on a surface comprising: applying to said surface an active substance for inhibiting or preventing microbial growth on the surface, said active substance comprising a mineral flour having at least one catalyst precipitated on or bound to said mineral flour, said catalyst selected from the group consisting of:

brownstone (manganese dioxide), finely divided elementary palladium, and finely divided elementary ruthenium.

2. The method according to claim 1, wherein said mineral flour is selected from the group consisting of:

montmorillonite, illite, kaolin, basalt flour, diabase flour, phonolite flour, granite-gneiss flour, and granite pegmatite flour.

3. The method according to claim 1, wherein a resin is admixed with the active substance to form a resinous emulsion, wherein said resin is selected from the group consisting of:

copal resin, dammar resin, shellac resin, colophonium resin, sandarac resin, phenol-formaldehyde resin, urea-formaldehyde resin, melamine-formaldehyde resin, alkyd resin, polyester resin, and epoxy resin.

4. The method according to claim 1, wherein said active substance is applied to the surface to be protected as a constituent of a varnish, a coating, or a finish.

5. An active substance for preventing growth of microorganisms on surfaces, comprising a mineral flour having a catalyst precipitated on or bound to said mineral flour, said catalyst selected from the group consisting of:

brownstone (manganese dioxide), finely divided elementary palladium, and finely divided elementary ruthenium.

6. The active substance according to claim 5, wherein said mineral flour is selected from the group consisting of:

montmorillonite, illite, kaolin, basalt flour, diabase flour, phonolite flour, granite-gneiss flour, and granite pegmatite flour.

7. The active substance according to claim 5, wherein a resin is admixed with said active substance to form a resinous emulsion, wherein said resin is selected from the group consisting of:

copal resin, dammar resin, shellac resin, colophonium resin, sandarac resin, phenol-formaldehyde resin, urea-formaldehyde resin, melamine-formaldehyde resin, alkyd resin, polyester resin, and epoxy resin.

8. The active substance according to claim 5, wherein said active substance is a constituent of a varnish, a coating material, a paint, or a finish.

9. The active substance according to claim 5 wherein said active substance is a constituent of a synthetic material or rubber compound.

10. The active substance according to claim 8 wherein said finish is a textile finish.

11. A coating composition used for surface treatment or finish, having as an essential ingredient therein an active substance for preventing the growth of microorganisms on surfaces, said active substance comprising a mineral flour having at least one catalyst precipitated on or bound to said mineral flour, said catalyst selected from the group consisting of:

brownstone (manganese dioxide), finely divided elementary palladium, and finely divided elementary ruthenium.

12. The composition according to claim 11, wherein said mineral flour is selected from the group consisting of:

montmorillonite, illite, kaolin, basalt flour, diabase flour, phonolite flour, granite-gneiss flour, and granite pegmatite meal.

13. The composition according to claim 11, wherein a resin is admixed with said active substance to form a resinous emulsion, wherein said resin is selected from the group consisting of:

copal resin,
dammar resin,
shellac resin,
colophonium resin,
sandarac resin,
phenol-formaldehyde resin,
urea-formaldehyde resin,
melamine-formaldehyde resin,
alkyd resin,
polyester resin, and
epoxy resin.

14. The composition according to claim 11, wherein said composition is a varnish, a coating material, a paint, or a finish.

15. The composition according to claim 11, wherein said active substance is present in an amount of about 5 to 25 weight percent, based on 100 weight percent of the weight of the composition.

16. The composition according to claim 14 wherein said finish is a textile finish.

17. A method for preventing microbial growth on a surface comprising:

applying to said surface a resinous emulsion for inhibiting or preventing microbial growth on the surface, said resinous emulsion comprising an emulsion of a resin and an active substance which is a mineral flour having at least one catalyst precipitated on or bound to said mineral flour, said catalyst selected from the group consisting of:
brownstone (manganese dioxide),
finely divided elementary palladium, and
finely divided elementary ruthenium; and
said resin selected from the group consisting of:
copal resin,
dammar resin,
shellac resin,
colophonium resin,
sandarac resin,
phenol-formaldehyde resin,
urea-formaldehyde resin,
melamine-formaldehyde resin,
alkyd resin,
polyester resin, and
epoxy resin.

18. A composition for preventing growth of microorganisms on surfaces, comprising a resinous emulsion of:

a resin and an active substance which is a mineral flour having at least one catalyst precipitated on or bound to said mineral flour, said catalyst selected from the group consisting of:
brownstone (manganese dioxide),
finely divided elementary palladium, and
finely divided elementary ruthenium; and
said resin selected from the group consisting of:
copal resin,
dammar resin,
shellac resin,
colophonium resin,
sandarac resin,
phenol-formaldehyde resin,
urea-formaldehyde resin,
melamine-formaldehyde resin,
alkyd resin,
polyester resin, and
epoxy resin.

\* \* \* \* \*

UNITED STATES PATENT AND TRADEMARK OFFICE
CERTIFICATE OF CORRECTION

PATENT NO. : 5,713,987
DATED : February 3, 1998
INVENTOR(S) : Toni Gradl

It is certified that error appears in the above-indentified patent and that said Letters Patent is hereby corrected as shown below:

Column 2, between lines 17 and 18, insert --illite--.

Column 3, line 41 (claim 2), change "illire" to --illite--.

Signed and Sealed this

Second Day of June, 1998

Attest:

BRUCE LEHMAN

Attesting Officer

Commissioner of Patents and Trademarks